(12) United States Patent
Grant et al.

(10) Patent No.: US 8,357,794 B2
(45) Date of Patent: Jan. 22, 2013

(54) EXOPOLYSACCHARIDE (75) Inventors: Raymond Alan Grant, Fairfield, OH (US); Liam O'Mahony, County Cork (IE); Barbara Sheil, County Cork (IE)

(73) Assignee: The Procter & Gamble Company and Alimentary Health Limited, Cincinnati, OH (US)

( * ) Notice: Subject to any disclaimer, the term of this patent is extended or adjusted under 35 U.S.C. 154(b) by 313 days.

(21) Appl. No.: 12/451,250

(22) PCT Filed: May 2, 2008

(86) PCT No.: PCT/IE2008/000054
§ 371 (c)(1),
(2), (4) Date: Mar. 11, 2010

(87) PCT Pub. No.: WO2008/135959
PCT Pub. Date: Nov. 13, 2008

(65) Prior Publication Data
US 2011/0046084 A1 Feb. 24, 2011

Related U.S. Application Data (60) Provisional application No. 60/924,242, filed on May 4, 2007.

(51) Int. Cl.
*C08B 37/00* (2006.01)
*C07H 5/04* (2006.01)
*C07H 5/06* (2006.01)
*A01N 43/04* (2006.01)
*A61K 31/715* (2006.01)

(52) U.S. Cl. .............................. 536/53; 536/55.3; 514/54
(58) Field of Classification Search ........................ None
See application file for complete search history.

(56) References Cited

FOREIGN PATENT DOCUMENTS

| | | |
|---|---|---|
| EP | 0 201 332 | 11/1986 |
| FR | 2652590 | 4/1991 |
| WO | 00/42168 | 7/2000 |

OTHER PUBLICATIONS

PubMed, Autoimmune disorders, http://www.ncbi.nlm.nih.gov/pubmedhealth/PMH0001819/, pp. 1-12, May 3, 2009.*
Sollid, Nature Reviews Immunology, vol. 2, Sep. 2002, pp. 647-655.*
Kornman, Am J Clin Nutr 2006;83(suppl):475S-83S.*
The Merck Manuals Online, Rheumatoid Arthritis, pp. 1-11, Feb. 2008.*
PubMed Health, Crohn's Disease, pp. 1-14, Dec. 13, 2011.*
Kalelkar et al. Carbohydrate Research 299 (1997) 119-128.*
International Search Report dated Jul. 16, 2008.

* cited by examiner

*Primary Examiner* — Layla Bland
(74) *Attorney, Agent, or Firm* — Amanda T. Barry (57) ABSTRACT

An isolated polysaccharide has the structure [-β(1,3)-D-GalpNAc-β(1,4)-D-Glcp-]$_n$ The polysaccharide may be from a *Bifidobacterium* strain NCIMB41003. The polysaccharide exhibits immunomodulatory activity.

13 Claims, 5 Drawing Sheets

Fig. 1

[ -β(1,3)-D-Gal*p*NAc - β(1,4)-D-Glc*p*- ]$_n$

EXOPOLYSACCHARIDE

This is a national stage of PCT/IE08/000,054 filed May 2, 2008 and published in English, claiming benefit of U.S. provisional application No. 60/924,242, filed May 4, 2007, hereby incorporated by reference.

FIELD OF THE INVENTION

The present invention relates to an exopolysaccharide, and to its use in treating and preventing inflammatory disorders.

BACKGROUND OF THE INVENTION

The gastrointestinal tract provides a protective interface between the internal environment and the constant challenge from food-derived antigens and from microorganisms in the external environment (Sanderson et al., 1993). The complex ecosystem of the adult intestinal microflora is estimated to harbor 500 different bacterial species. Some of these species are considered potentially harmful because of toxin production, mucosal invasion; or activation of carcinogens and inflammatory responses (Salminen, 1998). However, bacterial strains with health promoting activities have been identified.

Probiotics are beneficial bacteria that exist in the healthy gut microflora and have been defined as a group of live microbial organisms which beneficially affects a host animal by improving its intestinal microbial balance. They consist of "friendly bacteria" which are cultured in laboratory conditions and are then used to restore the balance of the microflora, which has become unbalanced because of, for example stress, illness, or as a result of the use of antibiotics. Importantly, it has been shown that the ingestion of probiotic bacteria can potentially stabilise the immunologic barrier in the gut mucosa by reducing the generation of local proinflammatory cytokines (Isolauri, 1993; Majamaa, 1997). Alteration of the properties of the indigenous microflora by probiotic therapy was shown to reverse some immunologic disturbances characteristic of Crohn's disease (Malin, 1996), food allergy (Majamaa, 1997), and atopic eczema (Isolauri, 2000).

One of the predominant bacterial species present in the intestinal microflora is *Bifidobacterium*. In the intestines, *Bifidobacterium* ferments sugars to produce lactic acid. The *Bifidobacterium longum* genome codes for many proteins specialised for the catabolism of oligosaccharides, enabling the bacterium to use so-called "nondigestible" plant polymers or host-derived glycoproteins and glycoconjugates. It is thought that *Bifidobacterium's* ability to compete with other gastrointestinal bacteria and occupy a large percentage in the bacterial flora of the gastrointestinal region might be partly due to the large variety of molecules that it is able to use for energy.

While *B. infantis, B. breve*, and *B. longum* are the largest bacteria group in the intestines of infants, Bifidobacteria are said to be only the 3rd or 4th largest group of bacteria in adults (and only 3-6% of adult fecal flora). The number of these bacteria actually decline in the human body with age. In infants who are breast-fed, Bifidobacteria constitute about 90% of their intestinal bacteria; however, this number is lower in bottle-fed infants. When breast-fed infants' diets are changed to cows milk and solid food, Bifidobacteria are joined by rising numbers of other bacteria found in the human body such as *Bacteroides* and *Streptococci lactobacilli*.

Bifidobacteria have been shown to play a role in the modulation of the immune system. *B. breve* is thought to release metabolites exerting an anti-TNF effect capable of crossing the intestinal barrier. Mucosal inflammation in interlukin-10 (IL-10) deficient mice has been reported to be reduced by feeding the subject animals a preparation of lactic acid bacteria (Madsen, K et al., 1997; O'Mahony et al., 2001; McCarthy et al., 2004). W0 00/41168 discloses a strain of *Bifidobacterium infantis* isolated from resected and washed human gastrointestinal tract which is significantly immunomodulatory following oral consumption in humans.

Scientific research indicates an increasing incidence of illness which may be caused by deficient or compromised microflora (natural microbial resident population of the digestive system) such as gastrointestinal tract (GIT) infections, constipation, irritable bowel syndrome (IBS), inflammatory bowel disease (IBD), Crohn's disease and ulcerative colitis, food allergies, antibiotic-induced diarrhoea, cardiovascular disease and certain cancers such as colorectal cancer. Evidence indicates that following treatment with a single *Bifidobacterium infantis* strain, IBS symptom severity is reduced (Whorwell et al., 2006). Efficacy is associated with modulation of systemic immune responses indicating that the mechanism of action, in part, is immune mediated (O'Mahony et al., 2005). The present invention describes a compound isolated from *Bifidobacterium infantis* that replicates the immunomodulatory activity of *Bifidobacterium infantis* in vitro.

STATEMENTS OF THE INVENTION

The present invention provides an polysaccharide produced by *Bifidobacterium infantis* which shows immunomodulatory properties. The polysaccharide may be secreted (exopolysaccharide) or non-secreted.

According to one aspect of the invention there is provided an isolated polysaccharide comprising the structure: $[-\beta(1,3)\text{-D-GalpNAc-}\beta(1,4)\text{-D-Glcp-}]_n$.

The polysaccharide may be isolated from a bacterial *Bifidobacterium* strain. The strain may be a strain such as NCIMB 41003.

According to another aspect of the invention there is provided use of a polysaccharide of the invention as a medicament.

According to another aspect of the invention there is provided use of a polysaccharide of the invention in the preparation of a medicament for treating or preventing undesirable inflammatory activity.

According to another aspect of the invention there is provided use of a polysaccharide of the invention in the preparation of a medicament for treating or preventing undesirable gastrointestinal inflammatory activity.

In one embodiment the gastrointestinal inflammatory activity is Crohn's disease, ulcerative colitis, irritable bowel syndrome, pouchitis, post infection colitis, *Clostridiuni difficile* associated diarrhoea, Rotavirus associated diarrhoea or post infective diarrhoea.

According to another aspect of the invention there is provided use of a polysaccharide of the invention in the preparation of a medicament for treating or preventing rheumatoid arthritis.

According to another aspect of the invention there is provided use of a polysaccharide of the invention in the preparation of a medicament for treating or preventing autoimmune disorders.

According to another aspect of the invention there is provided a pharmaceutical composition comprising a polysaccharide of the invention and a pharmaceutically acceptable carrier.

In a further embodiment the invention also provides a foodstuff comprising the isolated polysaccharide. For example the foodstuff may be one or more selected from the group comprising: yogurts, cereals, beverages and the like.

DETAILED DESCRIPTION

Various preferred features and embodiments of the present invention will now be described by way of non-limiting example.

The practice of the present invention will employ, unless otherwise indicated, conventional techniques of chemistry, microbiology and immunology, which are within the capabilities of a person of ordinary skill in the art. Such techniques are explained in the literature.

We have identified a *Bifidobacterium* secreted exopolysaccharide which has immuomodulatory properties.

Exopolysaccharide

The present invention relates to an exopolysaccharide biosynthesised by *Bifidobacterium infantis*. Polysaccharides are synthesised by a wide variety of micro-organisms and are usually repeating sugar units which remain associated with the cell surface or are secreted or both. They play a role in both cellular stress responses or can contribute to the virulence of a pathogen. Recently, an immunomodulatory role for *Bacteroides fragilis* polysaccharide has been demonstrated (Mazmanian et al., 2005).

Treatment

It is to be appreciated that all references herein to treatment include curative, palliative and prophylactic treatment. The treatment of mammals is particularly preferred. Both human and veterinary treatments are within the scope of the present invention.

Inflammation

Inflammation is a local response to cellular injury that is marked by capillary dilatation, leukocytic infiltration, redness, heat, pain, swelling, and often loss of function. Control of the inflammatory response is exerted on a number of levels (for review see Henderson B., and Wilson M. 1998. The controlling factors include cytokines, hormones (e.g. hydrocortisone), prostaglandins, reactive intermediates and leukotrienes.

Cytokines are low molecular weight biologically active proteins that are involved in the generation and control of immunological and inflammatory responses, while also regulating development, tissue repair and haematopoiesis. They provide a means of communication between leukocytes themselves and also with other cell types. Most cytokines are pleiotrophic and express multiple biologically overlapping activities.

Cytokine cascades and networks control the inflammatory response rather than the action of a particular cytokine on a particular cell type (Arai K I, et al., 1990). Waning of the inflammatory response results in lower concentrations of the appropriate activating signals and other inflammatory mediators leading to the cessation of the inflammatory response. Tumor narcrosis factor alpha (TNFα) is a pivotal proinflammatory cytokine as it initiates a cascade of cytokines and biological effects resulting in the inflammatory state. Therefore, agents which inhibit TNFα are currently being used for the treatment of inflammatory diseases, e.g. infliximab.

Pro-inflammatory cytokines are thought to play a major role in the pathogenesis of many inflammatory diseases, including inflammatory bowel disease (IBD). Current therapies for treating IBD are aimed at reducing the levels of these proinflammatory cytokines. The exopolysaccharide of the present invention may have potential application in the treatment of inflammatory disorders. This may be achieved, for example, by increasing the concentration of non-inflammatory cytokines such as, but not limited to IL-10, and/or decreasing the concentration of inflammatory cytokines.

Inflammatory Bowel Disease

Inflammatory bowel disease (IBD) is characterised by a chronic relapsing intestinal inflammation. IBD is subdivided into Crohn's disease and ulcerative colitis phenotypes. Crohn's disease may involve any part of the gastrointestinal tract, but most frequently the terminal ileum and colon. In approximately 10% of cases confined to the rectum and colon, definitive classification of Crohn's disease or ulcerative colitis cannot be made and are designated 'indeterminate colitis.' Both diseases include extra-intestinal inflammation of the skin, eyes, or joints.

Crohn's disease and ulcerative colitis are commonly classified as autoimmune diseases as both illnesses are marked by an abnormal response by the body's immune system resulting in chronic inflammation in the lining of the intestines. The prevalence of inflammatory bowel disease is increased in individuals with other autoimmune diseases, particularly ankylosing spondylitis, psoriasis, sclerosing cholangitis, and multiple sclerosis.

Crohn's Disease

Crohn's disease is a chronic disorder that causes inflammation of the digestive or gastrointestinal wherein the immune system attacks the intestine.

Although Crohn's disease most commonly affects the end of the ileum and the beginning of the colon, it may involve any part of the gastrointestinal tract. Bowel inflammation is transmural and discontinuous; it may contain granulomas or be associated with intestinal or perianal fistulas. The CARD15 gene and an allele of the ABCB1 gene are thought to be associated with susceptibility to Crohn's disease.

Ulcerative Colitis

Ulcerative colitis is a disease that causes inflammation and sores in the lining of the large intestine. It is a nonspecific chronic inflammatory disease affecting the bowel. Ulcers form and bleed in places where the inflammation has killed the cell lining. In contrast to Crohn's disease, the inflammation is continuous and limited to rectal and colonic mucosal layers; fistulas and granulomas are not observed.

Both genetic and environmental factors seem to be important in its etiology. Fuss et al. examined lamina propria T cells from patients with ulcerative colitis and found that they produced significantly greater amounts of IL13 and IL5 than control or Crohn's disease cells and little IFN-gamma. They concluded that ulcerative colitis is associated with an atypical Th2 response mediated by nonclassic NKT cells that produce IL13 and have cytotoxic potential for epithelial cells.

Pouchitis

Chronic and/or acute inflammation of the ileal reservoir, so-called "pouchitis", is a frequently observed long-term complication of the ileo-anal pouch anastomosis. In ulcerative colitis patients, the prevalence of pouchitis varies from less than 10% to higher than 40%. The definition of "pouchitis" includes clinical symptoms, macroscopic inflammatory lesions at endoscopy and histological evidence of intense acute inflammation of the reservoir mucosa.

*Clostridium difficile* Associated Diarrhoea

*Clostridium difficile* is an anaerobic, gram-positive spore forming bacillus first isolated in 1935 from faecal flora of healthy neonates. It was not until 1978 that its association with antibiotic induced pseudomembranous colitis (PMC) was established. Almost all antibiotics have been linked with *C. difficile* diarrhoea and colitis, including vancomycin and metronidazole (which are used for its treatment) and cancer chemotherapy. The frequency of association is related to frequency of use, the route of administration and the impact of that antibiotic on the colonic microflora.

Irritable Bowel Syndrome

Irritable bowel syndrome (IBS) is a chronic disorder that interferes with the normal functions of the large intestine (colon). It is characterised by a group of symptoms—crampy abdominal pain, bloating, constipation, and diarrhoea.

IBS causes a great deal of discomfort and distress, but it does not permanently harm the intestines and does not lead to intestinal bleeding or to any serious disease such as cancer. Signs and symptoms of IBS vary widely from one person to another and often occur with many other diseases.

Other Active Ingredients

It will be appreciated that the exopolysaccharide of the present invention may be administered prophylactically or as a method of treatment either on its own or with other probiotic and/or prebiotic materials. In addition, the bacteria may be used as part of a prophylactic or treatment regime using other active materials such as those used for treating inflammation or other disorders, especially those of the gastrointestinal tract. Such combinations may be administered in a single formulation or as separate formulations administered at the same or different times and using the same or different routes of administration.

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in a mixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Further preferred features and embodiments of the present invention will now be described by way of non-limiting example and with reference to the accompanying figures.

The strain *Bifidobacterium* 35624 (NCIMB 41003) strain is described in WO 00/42168, the entire contents of which are incorporated herein by reference. The strain was deposited at the NCIMB on Jan. 13, 1999.

Example 1

Purification and Structure Determination of the Exopolysaccharide (PS1) from the Conditioned Media Produced by *Bifidobacterium* 35624

Purification. 100 ml of sterile MRS media (CM359 MRS Broth, Oxoid Ltd., Basingstoke, Hampshire, England) supplemented with 0.05% (w/v) cysteine was placed into a sterile 250 ml Erlenmeyer flask inoculated with *Bifidobacterium* 35624. The inoculated media was incubated under anaerobic conditions (10-01 Pack-Anaero, Mitsubishi Gas Chemical Company-America, New York, N.Y.) at 37° C. without shaking. An uninoculated MRS media sample was used as a Media Control and was processed identically to the inoculated sample throughout the procedures outlined below.

After 48 hr of growth, the *Bifidobacterium* 35624 culture had reached stationary phase and displayed an OD 600 nm of about 3 ($2\text{-}3\times10^9$ colony forming units/ml). The cultures were transferred to polycarbonate centrifuge tubes and centrifuged at 40,000×g for 30 min (JA-20 rotor, Beckman J2-21 centrifuge, Beckman Coulter, Inc., Fullerton, Calif.), resulting in a clear supernatant and a tight cell pellet. The supernatant (conditioned media) was carefully removed and used in the purification of the exopolysaccharide (EPS). The cell pellet was discarded.

Figure 1:
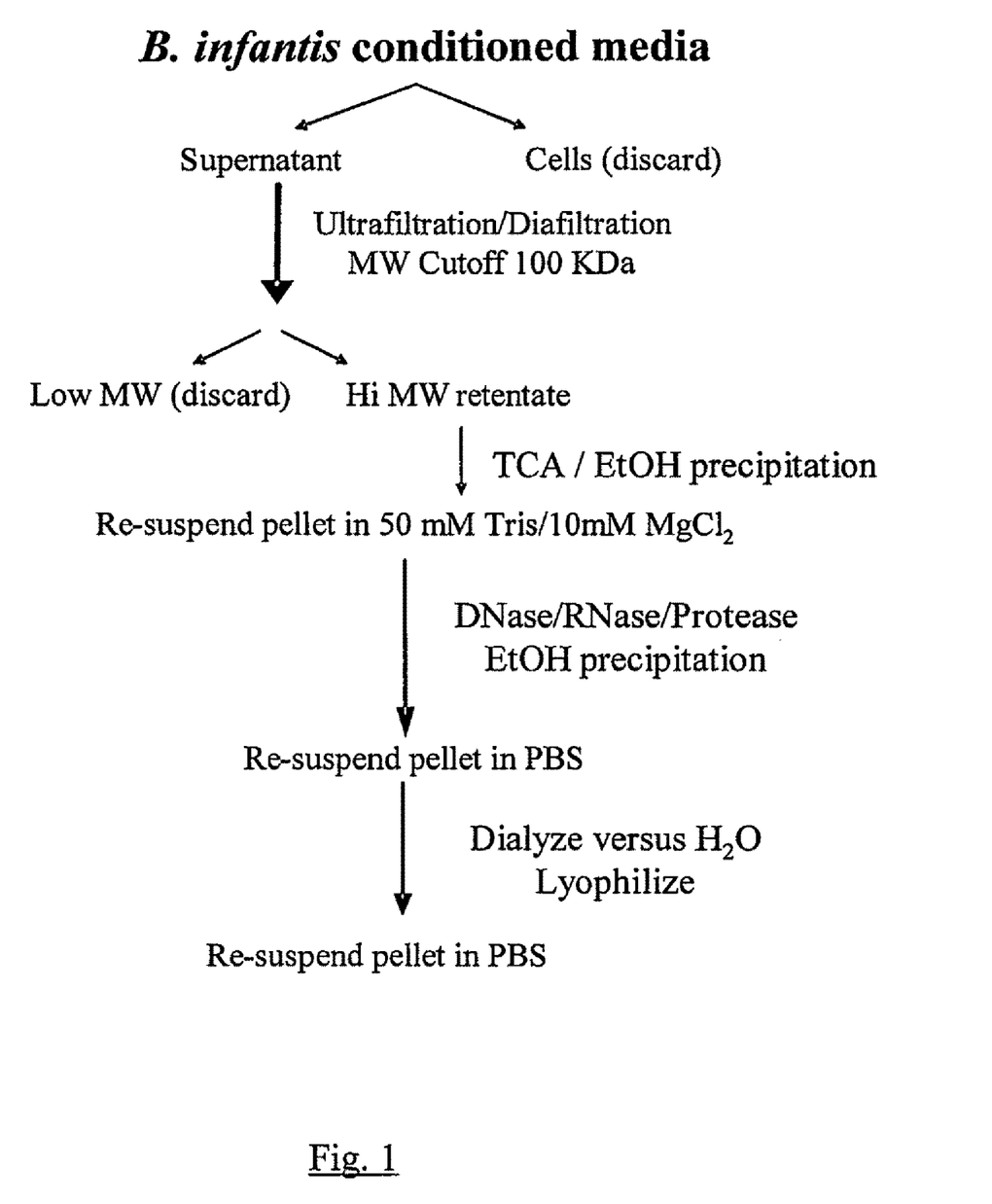
FIG. 1 shows the purification scheme for exopolysaccharide (PS1) from the conditioned media produced by *Bifidobacterium* 35624 (NCIMB 41003).

The purification scheme for the EPS from the conditioned media produced by *Bifidobacterium* 35624 is shown in FIG. 1. Unless mentioned otherwise, all steps were carried out on ice or at 4° C. 80 ml of the culture supernatant were loaded into an ultrafiltration device having a molecular weight (MW) cutoff of 100,000 Daltons (VC1042 Vivacell 100 ml concentrator, Vivascience, Hannover, Germany). The samples were concentrated by centrifugation at 2000×g in a clinical centrifuge. After the volume reached about 0.5 ml, the retentate (HiMW fraction) was diafiltered once using phosphate-buffered saline (PBS) and concentrated back down to about 0.5 ml. The retentate was transferred to a standard 15 ml centrifuge tube. The ultrafiltration device was rinsed with 4 ml of PBS, and this wash was pooled with the retentate to yield the HiMW retentate fraction.

A solution of 100% trichloroacetic acid (TCA) was added to the HiMW retentate fraction to a final concentration of 20% (v/v) TCA. Samples were incubated for 2 hr on ice and then centrifuged at 8000×g for 20 min (JA-20 rotor). The supernatant containing the EPS was transferred to a 30 ml Corex tube. The pellet that contained proteins was discarded. The supernatant containing the EPS was treated with 3 volumes of ice cold 95% ethanol and incubated overnight at −20° C. The tubes then were centrifuged at 8000×g for 20 min (JA-20 rotor). The supernatant was discarded. The pellet containing the EPS was resuspended in 5 ml of PBS and then precipitated again with 3 volumes of ethanol, as above. The pellet was air dried on ice for 60 min and then was resuspended in 9 ml of 10 mM MgCl2; 50 mM Tris-HCl (pH 7.4).

In order to remove nucleic acids, deoxyribonuclease I (LS006331, Worthington Biochemical Corporation, Lakewood, N.J.) and ribonuclease A (R5250, Sigma-Aldrich Corporation, St. Louis, Mo.) were each added to final concentrations of 0.1 mg/ml and incubated for 2 hr at 37° C. Residual proteins were removed by adding proteinase K (P2308, Sigma-Aldrich) to a final concentration of 0.02 mg/ml and then incubating the mixture for 2 hr at 37° C. Proteinase K was inactivated by incubation for 15 min at 70° C., followed by the addition of phenylmethylsulfonyl fluoride (P7626, Sigma-Aldrich) to a final concentration of 0.2 mM for 15 min at room temperature. The purified EPS was precipitated from solution by the addition of 3 volumes of ethanol, as above. The pellet was resuspended in 9 ml of phosphate-buffered saline. The resuspended sample was loaded into SnakeSkin dialysis tubing (68035, Pierce Biotechnology, Rockford, Ill.) having a molecular weight cutoff of 3500 and then dialyzed against 7 liters of water (2 changes) for 48 hr at 4° C.

A small aliquot of the dialyzed sample was removed for quantitation of the amount of polysaccharide present using the standard phenol/sulfuric acid method of Dubois et al. (Anal. Chem. 28, 350-356 (1956)). Once the concentration of the EPS was determined, appropriate aliquots were made, frozen on dry ice, and lyophilized to dryness. Lyophilized material was stored at −80° C.

NMR analyses. Proton nuclear magnetic resonance ($^1$H-NMR) analyses were performed on a Varian Inova 600-MHz spectrometer (Varian Medical Systems, Palo Alto, Calif.). Lyophilized samples were dissolved in $D_2O$, and after allowing for extensive exchange of deuterium, the spectra were obtained at 25° C. Chemical shifts were referenced to internal TSP. $^1$H-$^1$H correlation spectroscopy (COSY), total correlation spectroscopy (TOCSY), nuclear Overhauser effect spectroscopy (NOESY) and proton-carbon heteronuclear single quantum correlation spectroscopy (HSQC) data were collected in phase-sensitive modes using States-Haberkom-Rubin quadrature. All pulse sequences were supplied by the spectrometer vendor and used without modification. Low-power presaturation was applied to the residual HDO signal. Typically, data sets were collected with 512 times 2,048 complex data points, and 16-32 scans/increment. The TOCSY pulse program contained a 60-ms MLEV-17 mixing sequence, and the NOESY mixing time was 150 ms.

Carbohydrate analyses. Glycosyl composition analyses were performed by combined gas chromatography/mass spectrometry (GC/MS) of the per-O-trimethylsilyl (TMS) derivatives of the monosaccharide methyl glycosides produced from the purified Bifidobacterium 35624 EPS by acidic methanolysis (York et al., (1986); Merkle, R. K. and Poppe, I. 1994). For glycosyl linkage analysis, the EPS sample was permethylated, depolymerized, reduced, and acetylated. The resultant partially methylated alditol acetates (PMAAs) were analyzed by GC-MS as described previously (York et al, (1986); Merkle and Poppe (1994)).

Structure Determination of the EPS.

Figure 2:
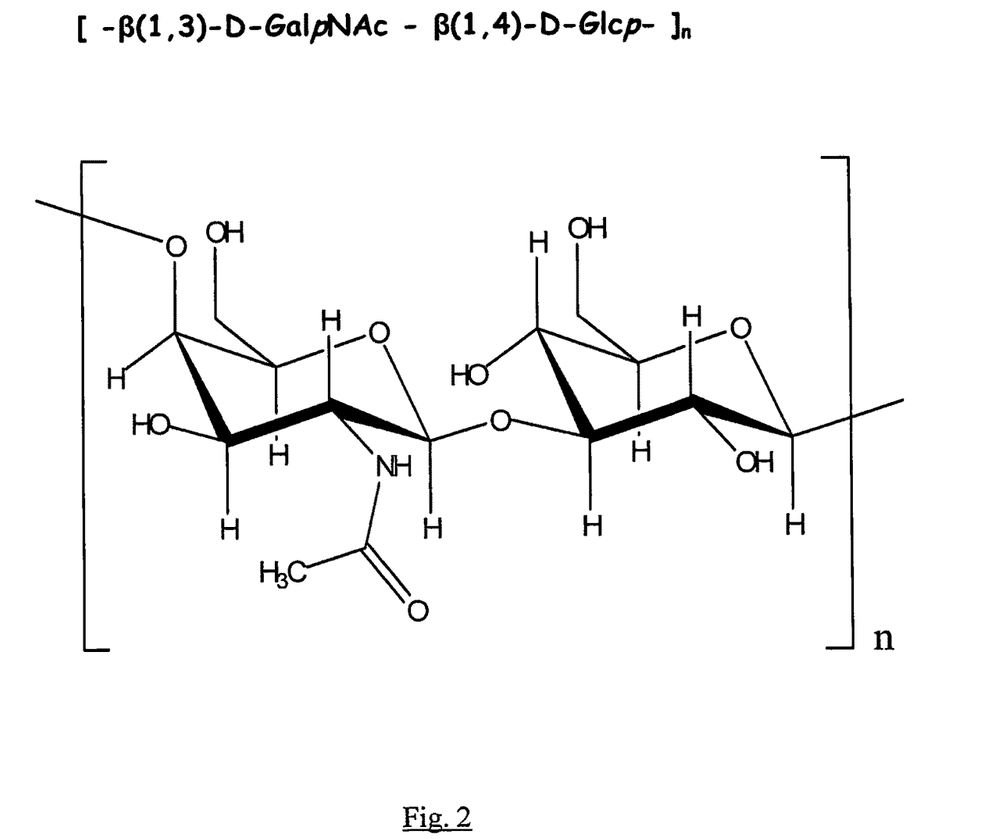
FIG. 2 shows the structure of the exopolysaccharide (PS1) produced by *Bifidobacterium* 35624 (NCIMB 41003).

The purified EPS was analysed using $^1$H-NMR. The spectra showed that this material was composed exclusively of carbohydrate; there was no indication of nucleic acid, protein, lipid, or small organic contaminants. Two-dimensional NMR (2D-NMR) analyses using experiments known in the art and described above established that the majority of the carbohydrate present comprised a linear polysaccharide that consists of disaccharide repeats. Combined with data from the composition and linkage analyses, the structure of this polysaccharide (named PS1) is [-β(1,3)-linked-D-N-acetyl-galactosamine pyranosyl-β(1,4)-linked-D-glucose pyranosyl-]$_n$, where n indicates that this disaccharide unit is repeated n times, giving a polysaccharide having a molecular weight of greater than 100,000 Daltons. The structure of PS1 can be abbreviated as [-β(1,3)-D-GalpNAc-β(1,4)-D-Glcp-]$_n$ and is shown in FIG. 2. Note that PS1 was not detected in the Media Control sample.

Example 2

B. infantis 35624 Exopolysaccharide (PS1) has Immunomodulatory Activity when Co-Incubated with Human Immune System Cells In Vitro EPS fractions were assayed using the PBMC (peripheral blood mononuclear cell) cytokine induction assay. In this assay, PBMCs are isolated from blood by density gradient separation and incubated for 72 hours at 37° C. (in the presence of penicillin and streptomycin) with control media, or with increasing concentrations of purified PS1 from B. infantis 35624. Supernatants were assayed for IL-1β, IL-6, IL-8, IL-10, IL-12, TNF-α and IFN-γ levels using mesoscale discovery (MSD) kits and analysed using an MSD plate reader.

Figure 3:
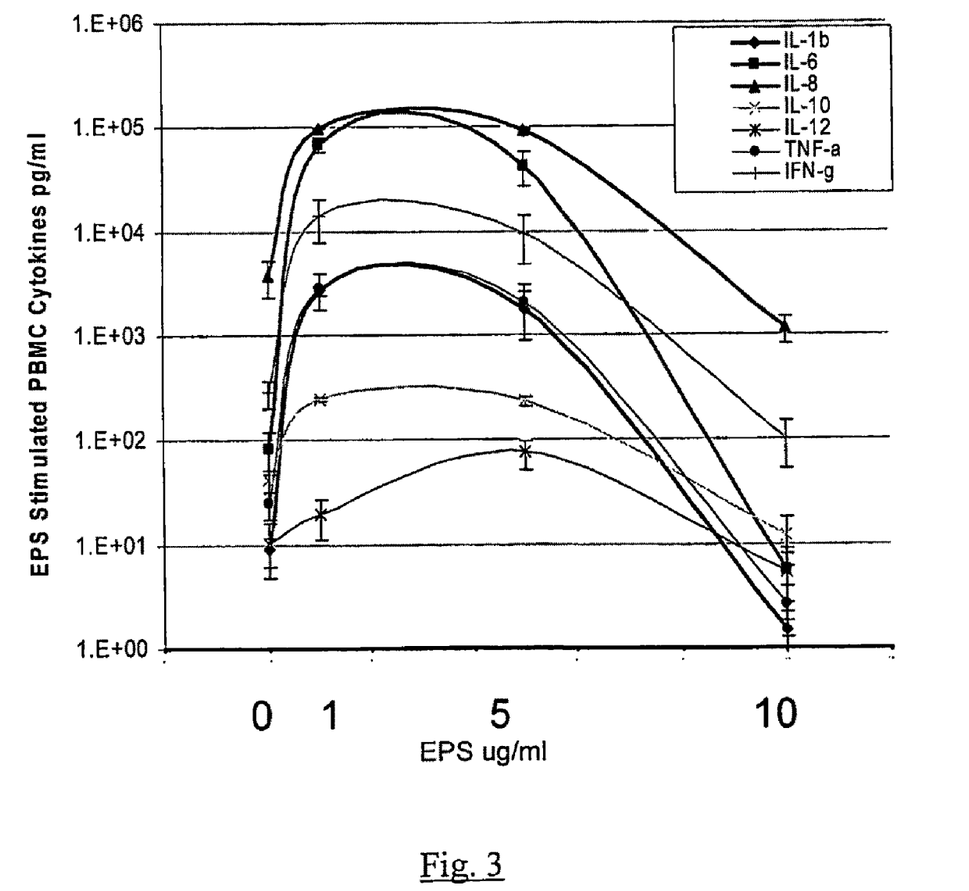
FIG. 3 illustrates that the purified exopolysaccharide (PS1) from *Bifidobacterium* 35624 [NCIMB 41003] exhibits immunomodulatory activity when co-incubated in vitro with human peripheral blood mononuclear cells.

FIG. 3 illustrates the results of this assay. PS1 stimulated the secretion of all cytokines tested when PBMCs were stimulated with 1-5 μg/ml PS1. The cytokine stimulatory activity was reduced to background levels for many cytokines when 10 μg/ml PS1 was used.

Figure 4:
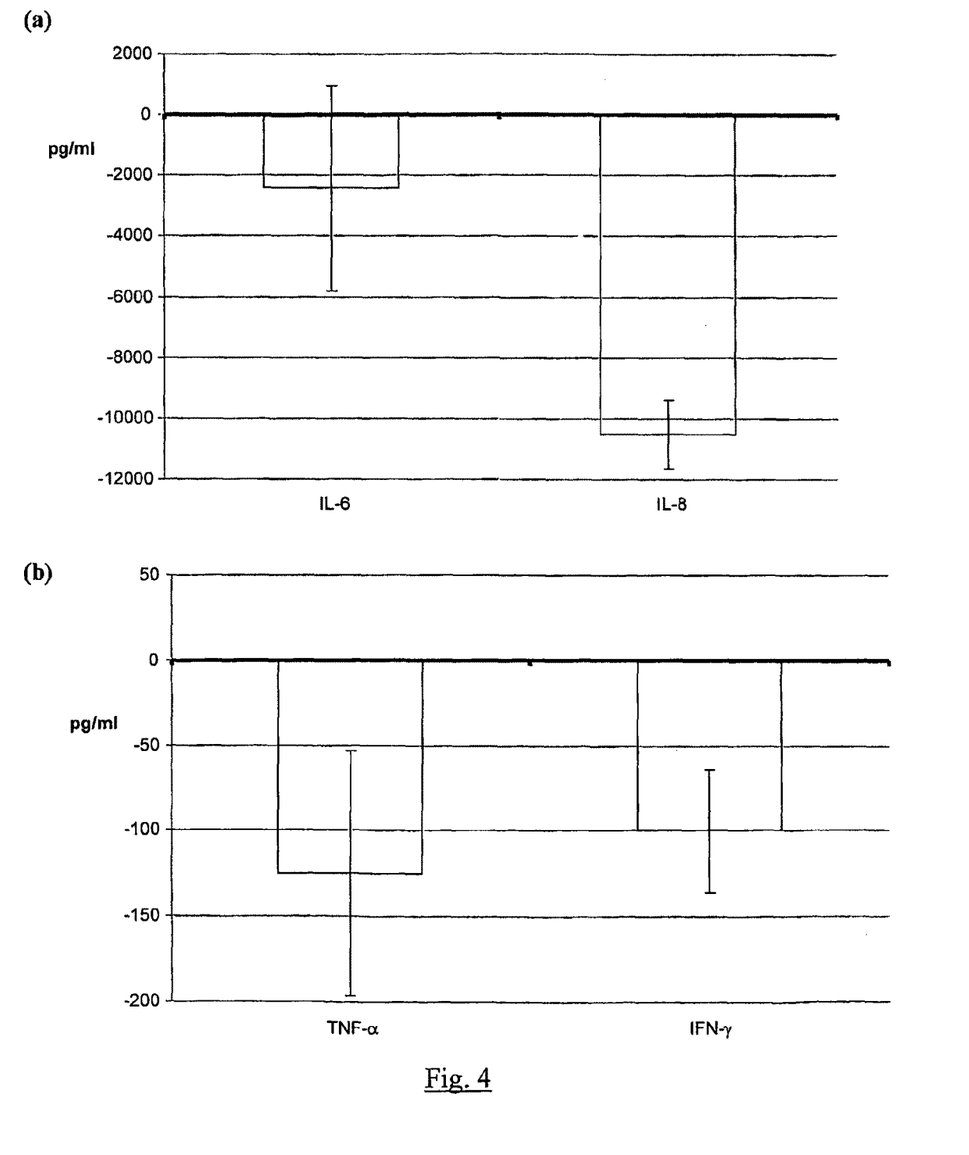
FIG. 4 demonstrates that PS1 limits pro-inflammatory cytokine release in response to Toll-like receptor 4 (TLR-4) stimulation in vitro.

In addition to testing resting PBMCs, the TLR-4 ligand lipopolysaccharide (LPS) was used to activate PBMCs with or without PS1 stimulation. As 5 μg/ml PS1 was observed to be an optimal dose in preliminary experiments, this dose was used in subsequent assays. These results are illustrated in FIG. 4 as the mean cytokine value for LPS+PS1 stimulated cells minus the cytokine value for cells stimulated with LPS alone. When co-incubated with PS1, LPS stimulated PBMCs secrete substantially less IL-6 and significantly less IL-8, TNF-α and IFN-γ.

Example 3

Figure 5:
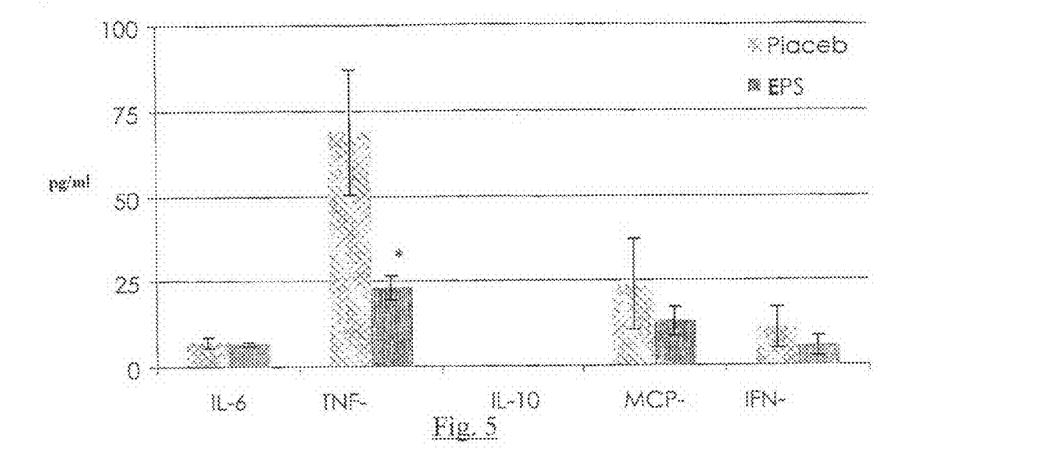
FIG. 5 demonstrates that PS1 limits pro-inflammatory cytokine release in response to Toll-like receptor 4 (TLR-4) stimulation in vivo.
Figure 6:
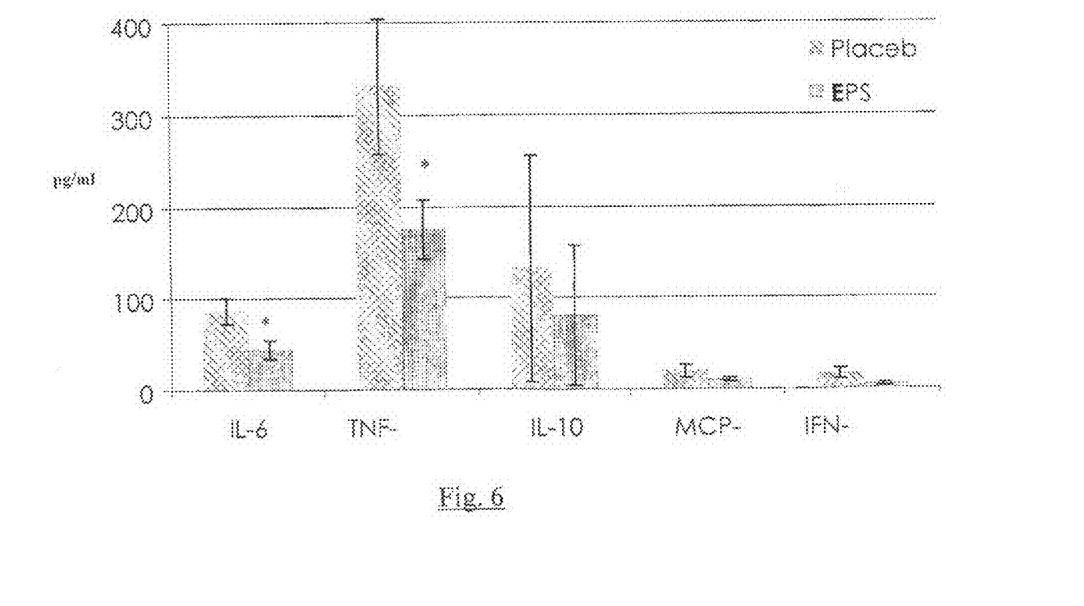
FIG. 6 demonstrates that PS1 limits pro-inflammatory cytokine release in response to Toll-like receptor 4 (TLR-4) re-stimulation in vitro.

B. infanta 35624 Exopolysaccharide (PS1) has Anti-Inflammatory Activity when Injected into a Murine Model of Sepsis PS1 was injected i.p. into healthy mice and these mice were observed for 24 hours. No obvious signs of distress were noted suggesting that this polysaccharide was well tolerated by the animals and PS1 did not induce sepsis or a pro-inflammatory response. Following the 24 hour observation period, animals were injected i.p. with lipopolysaccharide (LPS) in order to induce a sepsis-like response. All animals were culled 2 hours later and splenocyte cytokine secretion measured in vitro. Splenocytes isolated from PS1+LPS treated mice released significantly less TNF-α when compared to mice that received LPS alone (FIG. 5). In addition, splenocytes from these animals were re-stimulated with LPS in vitro and again a blunted proinflammatory cytokine response was noted in splenocytes derived from animals previously exposed to PS1 (FIG. 6).

Taken together, these data demonstrate that EPS1, derived from *Bifidobacterium infantis* 35624, has immunomodulatory activity and protects against LPS or TLR-4 mediated inflammatory responses.

Whilst the experimentation above describes the secreted exopolysaccharide (PS1) it is envisaged that a non-secreted form of the exopolysaccharide, for example a cell associated or membrane associated/bound or capsular form of the exopolysaccharide, would behave in a similar way to the secreted EPS. The experimentation described herein was designed to examine the secreted EPS but it will be apparent to a person skilled in the art that a proportion of the secreted EPS may bind to the cell (for example cell associated or capsular) during manufacture of the EPS and prior to the transport or release of the EPS from the cell.

The invention is not limited to the embodiments hereinbefore described which may be varied in detail.

REFERENCES

Arai K I, et al., Annu Rev Biochem 59: 783-836, 1990
Fuss et al., "Nonclassical CD1d-restricted NK T cells that produce IL-13 characterize an atypical Th2 response in ulcerative colitis." Inflamm Bowel Dis. 2005 January; 11(1):74-5
Henderson B., and Wilson M. In"Bacteria-Cytokine interactions in health and disease",
Isolauri et al., Clin Exp Allergy 30:1605-10, 2000
Isolauri et al. Pediatr Res. 33:548-53, 1993
Madsen et al., Gastroenterology 112:A1030, 1997
Majamaa et al., J Allergy Clin Immunol 99:179-86, 1997
Malin et al., Br J Rheumatol 35:689-94, 1996
McCarthy et al., Gut 53:694-700, 2004
Mazmanian et al., Cell 122:107-118, 2005
Merkle and Poppe Methods Enzymol. 230:1-15, 1994
O'Mahony et al., Aliment Pharmacol Ther 15:1219-25, 2001
O'Mahony et al., Gastroenterology 128:541-51, 2005
Portland Press, 79-130, 1998
Remington's Pharmaceutical Sciences, Mack Publishing Co. 1985 (Editor: A. R. Gennaro)
Salminen, Int J Food Microbiol 20:93-106, 1998
Sanderson et al., Gastroenterology 104:622-39, 1993
Whorwell et al., Am J Gastroenterol 101:1581-90, 2006
York et al., Methods Enzymol. 118:3-40, 1986

The invention claimed is:

1. An isolated polysaccharide comprising the structure $[-\beta(1,3)\text{-D-GalpNAc-}\beta(1,4)\text{-D-Glcp-}]_n$, wherein the structure is repeated n times to form a polysaccharide having a molecular weight of greater than 100,000 Daltons.

2. An isolated polysaccharide from a bacterial strain comprising the structure $[-\beta(1,3)\text{-D-GalpNAc-}\beta(1,4)\text{-D-Glcp-}]_n$, wherein the structure is repeated n times to form a polysaccharide having a molecular weight of greater than 100,000 Daltons.

3. An isolated polysaccharide from a *Bifidobacterium* strain comprising the structure $[-\beta(1,3)\text{-D-GalpNAc-}\beta(1,4)\text{-D-Glcp-}]_n$, wherein the structure is repeated n times to form a polysaccharide having a molecular weight of greater than 100,000 Daltons.

4. An isolated polysaccharide from *Bifidobacterium* strain NCIMB 41003 comprising the structure $[-\beta(1,3)\text{-D-GalpNAc-}\beta(1,4)\text{-D-Glcp-}]_n$, wherein the structure is repeated n times to form a polysaccharide having a molecular weight of greater than 100,000 Daltons.

5. A method for treating inflammation in a mammalian subject, the method comprising administering a polysaccharide comprising the structure $[-\beta(1,3)\text{-D-GalpNAc-}\beta(1,4)\text{-D-Glcp-}]_n$ to the subject, wherein the structure is repeated n times to form a polysaccharide having a molecular weight of greater than 100,000 Daltons.

6. A method for treating gastrointestinal inflammation in a mammalian subject, the method comprising administering a polysaccharide comprising the structure $[-\beta(1,3)\text{-D-GalpNAc-}\beta(1,4)\text{-D-Glcp-}]_n$ to the subject, wherein the structure is repeated n times to form a polysaccharide having a molecular weight of greater than 100,000 Daltons.

7. The method of claim 6, wherein the gastrointestinal inflammation is associated with Crohns disease, ulcerative colitis, irritable bowel syndrome, pouchitis, post infection colitis, Clostridium difficile associated diarrhoea, Rotavirus, associated diarrhoea or post infective diarrhoea.

8. A method of treating rheumatoid arthritis in a mammalian subject comprising administering a polysaccharide comprising the structure $[-\beta(1,3)\text{-D-GalpNAc-}\beta(1,4)\text{-D-Glcp-}]_n$ to the subject, wherein the structure is repeated n times to form a polysaccharide having a molecular weight of greater than 100,000 Daltons.

9. A composition comprising a polysaccharide as claimed in claim 1 and a pharmaceutically acceptable carrier.

10. A foodstuff comprising the polysaccharide of claim 1.

11. The foodstuff of claim 10, wherein the foodstuff is selected from the group consisting of a yogurt, a cereal, and a beverage.

12. The method of claim 7, wherein the polysaccharide is from *Bifidobacterium* strain NCIMB 41003.

13. The method of claim 8, wherein the polysaccharide is from *Bifidobacterium* strain NCIMB 41003.

* * * * *